US006606509B2

(12) United States Patent
Schmitt (10) Patent No.: US 6,606,509 B2
(45) Date of Patent: Aug. 12, 2003

(54) METHOD AND APPARATUS FOR IMPROVING THE ACCURACY OF NONINVASIVE HEMATOCRIT MEASUREMENTS

(75) Inventor: Joseph M. Schmitt, Andover, MA (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 12 days.

(21) Appl. No.: 09/811,328

(22) Filed: Mar. 16, 2001

(65) Prior Publication Data

US 2002/0165439 A1 Nov. 7, 2002

(51) Int. Cl.[7] ................................................. A61B 5/00
(52) U.S. Cl. ......................... 600/310; 600/322; 600/368
(58) Field of Search .............................. 600/310, 322, 600/323, 326, 335, 336, 368

(56) References Cited

U.S. PATENT DOCUMENTS

| | | | |
|---|---|---|---|
| 3,998,550 A | * 12/1976 | Konishi et al. ................ 356/39 |
| 4,883,055 A | 11/1989 | Merrick ....................... 128/633 |
| 4,907,594 A | 3/1990 | Muz ........................... 128/633 |
| 5,057,695 A | 10/1991 | Hirao et al. .................. 250/575 |
| 5,086,781 A | 2/1992 | Bookspan ..................... 128/734 |
| 5,111,817 A | * 5/1992 | Clark et al. ................... 356/41 |
| 5,224,478 A | 7/1993 | Sakai et al. .................. 128/633 |
| 5,277,181 A | 1/1994 | Mendelson et al. ......... 128/633 |
| 5,279,295 A | 1/1994 | Martens et al. ............. 128/633 |
| 5,282,467 A | 2/1994 | Piantadosi et al. .......... 128/633 |
| 5,337,745 A | 8/1994 | Benaron ..................... 128/633 |
| 5,348,004 A | 9/1994 | Hollub ....................... 128/633 |
| 5,355,880 A | * 10/1994 | Thomas et al. ............. 128/925 |
| 5,377,674 A | 1/1995 | Kuestner .................... 128/633 |
| 5,499,627 A | 3/1996 | Steuer et al. ............... 128/633 |
| 5,687,721 A | * 11/1997 | Kuhls ......................... 356/364 |
| 5,720,284 A | 2/1998 | Aoyagi et al. .............. 128/633 |
| 5,803,908 A | 9/1998 | Steuer et al. ............... 600/314 |
| 5,827,181 A | 10/1998 | Dias et al. .................. 600/322 |
| 5,833,602 A | 11/1998 | Osemwota |
| 5,853,364 A | 12/1998 | Baker, Jr. et al. ........... 600/300 |
| 5,860,919 A | * 1/1999 | Kiani-Azar |
| | | bayjany et al. ............. 600/310 |
| 6,064,898 A | * 5/2000 | Aldrich ...................... 600/316 |
| 6,178,342 B1 | 1/2001 | Borgos et al. |
| 6,222,189 B1 | * 4/2001 | Misner et al. ............. 250/341.1 |
| 6,400,971 B1 | * 6/2002 | Finarov et al. ............ 600/310 |
| 6,402,690 B1 | * 6/2002 | Rhee et al. ................. 128/903 |

FOREIGN PATENT DOCUMENTS

WO WO 93/13706 A2 7/1993

OTHER PUBLICATIONS

Schmitt et al., *Proc. SPIE*, "Measurement of blood hematocrit by dual–wavelength near–IR photoplethysmography," 1641:150–161 (1992).

Schmitt et al., *Proc. SPIE*, "Optimun wavelengths for measurement of blood hemoglobin content and tissue hydration by NIR spectrophotometry," 2678:442–453 (1996).

* cited by examiner

*Primary Examiner*—Alfred Rasichas
(74) *Attorney, Agent, or Firm*—Townsend & Townsend & Crew LLP (57) ABSTRACT

A device and a method to provide a more reliable and accurate measurement of hematocrit (Hct) by noninvasive means. The changes in the intensities of light of multiple wavelengths transmitted through or reflected light from the tissue location are recorded immediately before and after occluding the flow of venous blood from the tissue location with an occlusion device positioned near the tissue location. As the venous return stops and the incoming arterial blood expands the blood vessels, the light intensities measured within a particular band of near-infrared wavelengths decrease in proportion to the volume of hemoglobin in the tissue location; those intensities measured within a separate band of wavelengths in which water absorbs respond to the difference between the water fractions within the blood and the displaced tissue volume. A mathematical algorithm applied to the time-varying intensities yields a quantitative estimate of the absolute concentration of hemoglobin in the blood. To compensate for the effect of the unknown fraction of water in the extravascular tissue on the Hct measurement, the tissue water fraction is determined before the occlusion cycle begins by measuring the diffuse transmittance or reflectance spectra of the tissue at selected wavelengths.

27 Claims, 9 Drawing Sheets

METHOD AND APPARATUS FOR IMPROVING THE ACCURACY OF NONINVASIVE HEMATOCRIT MEASUREMENTS

BACKGROUND OF THE INVENTION

1. Field of the Invention

This invention relates to systems and methods for spectrophotometric measurement of biochemical compounds in the skin for non-invasive medical diagnosis and monitoring. Specifically, the present invention relates to the determination of the hematocrit or the absolute concentration of hemoglobin in the blood by multiple-wavelength optical plethysmography.

2. Discussion of Related Art

The total concentration of hemoglobin in blood ($Hb_T$) or the hematocrit (Hct), defined as the fraction or percentage of red cells in whole blood, are primary variables used by physicians to assess the health of a patient. The hematocrit is the fraction of the total blood volume occupied by the red blood cells, and hemoglobin is the principal active constituent of red blood cells. Approximately 34% of the red cell volume is occupied by hemoglobin. A value of $Hb_T$ less than 10 g/dl or Hct <0.30 indicates an anemic state which can impair the normal functions of the body. Severe anemia can lead to death when the quantity of hemoglobin becomes insufficient to supply oxygen to the brain and other vital organs. Patients with kidney disease, pregnant women, and young children in developing countries are especially susceptible to chronic anemia. Acute anemia resulting from loss of blood, infection, or autoimmune disorders can be life-threatening and requires close monitoring.

The conventional means employed to measure Hct in clinical medicine is to puncture the skin, draw blood from a vein or capillary into a small-diameter tube, and measure the solid (packed-cell) fraction that remains after centrifugation of the blood. Measurement of $Hb_T$ in accordance with standard practice also requires drawing a blood sample, which is then subjected to a chemical or mechanical process to lyse the red cells and release the liquid hemoglobin. After transferring the hemoglobin to a cuvette, its concentration is measured either by direct spectrophotometry or by colorimetry following the addition of a chemical reagent.

Although a number of methods have been developed to make these sampling and processing steps less cumbersome, no device is yet available to physicians for the reliable and accurate measurement of Hct or $Hb_T$ that obviates blood sampling.

A number of researchers and inventors have recognized the value of a completely noninvasive method for measurement of hematocrit or total hemoglobin concentration. Schmitt et al. (Proc. SPIE, 1992, Vol. 1641, pp. 150–161) adapted the principles of pulse oximetry to the noninvasive measurement of hematocrit of blood in intact skin. The method is based on the measurement of the ratios of the pulsatile (ac) and non-pulsatile (dc) components of the light transmitted through a blood-perfused tissue within two spectral bands in which the molar extinction coefficients of oxygenated hemoglobin ($HbO_2$) and deoxygenated hemoglobin (Hb) are nearly the same. In one of the wavelength bands ($800 \leq \lambda \leq 1000$ nm), the absorption of hemoglobin is the dominate contributor to the attenuation of light in blood; in the other band ($1200 \leq \lambda \leq 1550$ nm), the absorption of water dominates. Therefore, the absorption of water serves as a measure of the plasma (non-cellular) fraction of the blood which does not contain hemoglobin. A hematocrit monitoring system based on a similar method has been disclosed by Steuer et al. (U.S. Pat. No. 5,499,627). In this disclosure, the influence of the optical properties of extravascular interstitial fluid on the accuracy of the measurement was recognized and the addition of a third wavelength was proposed to reduce this influence. The concept of adding more wavelengths to improve accuracy was extended further by Kuenster (U.S. Pat. No. 5,377,674) and Aoyagi et al. (U.S. Pat. No. 5,720,284). Steuer et al. (U.S. Pat. No. 5,499,627) also recognized the difficulty of obtaining a reliable plethysmographic pulse in the water absorption band (its amplitude is typically 4–10 times smaller than in the hemoglobin absorption band). To alleviate this problem, Steuer et al. (U.S. Pat. No. 5,499,627) proposed a method for inducing an artificial pulse by mechanical compression of the tissue at the location of hematocrit measurements.

In spite of these earlier advances, measuring the absolute concentration of hemoglobin in blood accurately and reliably remains difficult in practice. This difficulty stems mainly from two limitations.

The first limitation is the failure of the available mathematical algorithms used in the prior art devices to account for the fact that the blood vessels displace the extravascular tissue when they expand, because the tissue is essentially incompressible. Because of the incompressibility of tissue, the change in the diffuse transmission of light through tissue observed during arterial pulsation depends on the difference between the optical properties of the blood and the surrounding gelatinous tissue matrix. Therefore, to obtain an accurate measure of the absolute values of the hemoglobin concentration in the blood, one must also account for the optical properties of the tissue that surrounds the blood vessels in the skin. Measurement of the ac/dc ratios alone, regardless of the number of wavelengths at which the measurement is made, cannot compensate entirely for the variations in the scattering and absorption properties of the skin of different subjects. This problem is not important in conventional pulse oximetry because the attenuation of light in blood greatly exceeds that in the surrounding tissue at the wavelengths at which ac/dc ratios are measured (typically 660 nm and 910 nm). The same is not true in the measurement of $Hb_T$ by optical plethysmography, however, which relies on the measurement of pulsations resulting from optical absorption of water in the blood. Because the volume fraction of water in blood is close to that of the extravascular tissue matrix, the difference between the absorptivities of blood and the surrounding tissue is small within water absorption bands. Moreover, the difference between the scattering properties of blood and the surrounding tissue vary with their relative water contents. Accordingly, one limitation of the prior art devices and methods used to noninvasively measure hematocrit or hemoglobin has been the inaccurate measurement of tissue water.

The second limitation is the reliance of the prior art methods on the measurement of small pulsatile changes in the blood volume induced by contractions of the heart. When the water contents of the blood and the extravascular tissues are nearly the same, the pulsatile (ac) component of intensities measured at wavelengths greater than 1250 nm are usually less than one percent of the mean (dc) intensity. Even using the most advanced circuitry and signal-processing techniques, the amplitudes of such small pulsations are difficult to measure reliably. Although mechanical compression of the tissue, as proposed by Steuer et al. (U.S. Pat. No. 5,499,627), alleviates this problem by inducing a larger blood volume change, it also introduces large changes in the scattering coefficient of the bulk tissue which can complicate calibration of instruments based on this technique, because the compression is occurring at the same location as where the hematocrit measurements are taken.

Therefore, there exist a need for more reliable and accurate measurement of hematocrit by noninvasive means.

SUMMARY OF THE INVENTION

The objective of embodiments of the present invention is to provide a more reliable and accurate measurement of hematocrit (Hct) by noninvasive means. The changes in the intensities of light of multiple wavelengths transmitted through or reflected light from a tissue location are recorded immediately before and after occluding the flow of venous blood from the tissue location with an occlusion device positioned near the tissue location. As the venous return stops and the incoming arterial blood expands the blood vessels, the light intensities measured within a particular band of near-infrared wavelengths decrease in proportion to the volume of hemoglobin in the tissue location; those intensities measured within a separate band of wavelengths in which water absorbs respond to the difference between the water fractions within the blood and the displaced tissue volume. A mathematical algorithm applied to the time-varying intensities yields a quantitative estimate of the absolute concentration of hemoglobin in the blood. To compensate for the effect of the unknown fraction of water in the extravascular tissue on the Hct measurement, the tissue water fraction is determined before the occlusion cycle begins by measuring the diffuse transmittance or reflectance spectra of the tissue at selected wavelengths.

An important feature of the embodiments of this invention is that it incorporates a means of compensating for natural variations in the water fraction of skin of different individuals. Such variations affect both the scattering and absorption coefficients of skin in the near-infrared region of the spectrum and are a primary source of error in hematocrit estimates derived from the assumption that the optical coefficients of the extravascular tissue are fixed quantities.

An equally important feature of the embodiments of this invention is that the relatively large change in blood volume induced by the venous occlusion facilitates the measurement of small differences between the optical properties of the blood and the extravascular tissue. Thus, better accuracy can be obtained compared to methods that rely on arterial blood pulsations. It should be understood, however, that the mathematical algorithm on which the present invention is based applies equally well to intensity changes induced by natural arterial pulsations or compression of the skin.

For a fuller understanding of the nature and advantages of the embodiments of the present invention, reference should be made to the following detailed description taken in conjunction with the accompanying drawings.

DESCRIPTION OF THE SPECIFIC EMBODIMENTS

Figure 1:
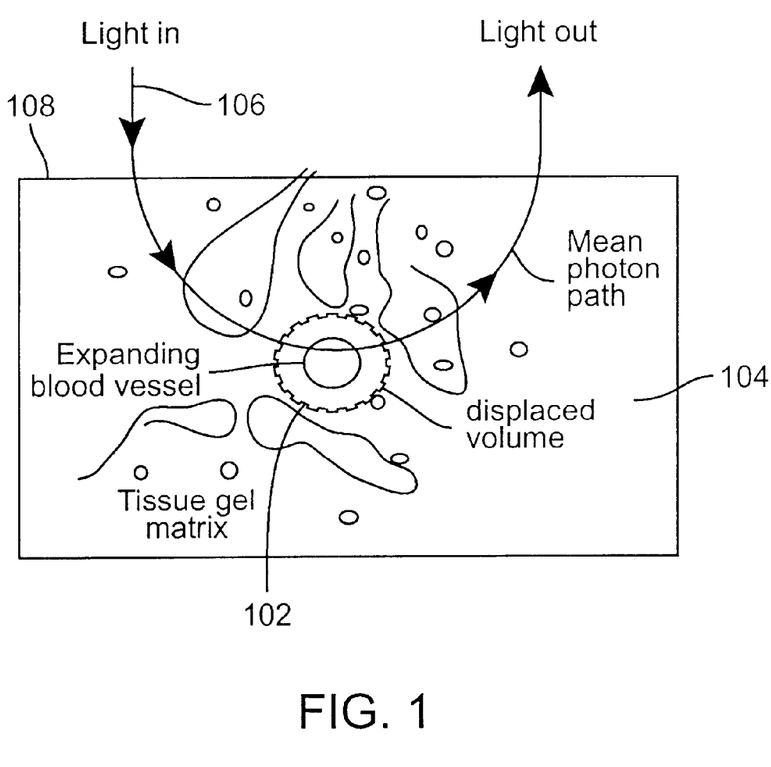
FIG. 1 is a diagram of an expanding blood vessel in the skin through which light scatters.

To understand the principles that underlie the invention, first consider a small blood vessel 102 embedded in the skin 104 on which light 106 impinges from the surface 108 as shown in FIG. 1. A fraction of the incident photons scatter through the blood before being captured by the detector. When the vessel 102 expands its volume, the probability of photons being absorbed or scattered by the blood inside the vessel increases. The absorption of the light that occurs within the volume probed by the light that reaches the detector (the effective sample volume) can be described approximately by a modified form of the Beer-Lambert law, which quantifies the diffusely reflected or transmitted intensity I before and after expansion of the vessel by an increase in the volume of blood $\Delta V$, (Before expansion) (1)

$$\log(1/I)_{dc} = \frac{\bar{l}}{V_T}(\mu_a^b V_b + \mu_a^t V_t)$$

(After expansion) (2)

$$\log(1/I)_{ac+dc} = \frac{\bar{l}}{V_T}[\mu_a^b(V_b + \Delta V) + \mu_a^t(V_t - \Delta V)]$$

where $\bar{l}$ is the effective length of the optical path between the source and detector, $V_T$ is the sample volume, and $V_t$ and $V_b$ are, respectively, the volumes of extravascular tissue and blood within $V_T$. The variables $\mu_a^b$ and $\mu_a^t$ represent the optical attenuation coefficients of the blood and the extravascular tissue, respectively. The second term in the brackets on the right side of Eq. 2 accounts for the displacement of the original volume of tissue by the same volume of blood, which leads to the observation that the difference between the log-transformed spectra before and after expansion (this differential spectrum is referred to as the 'blood pulse spectrum' in the remainder of this disclosure) depends on the difference between the optical attenuation coefficients of the blood and extravascular tissue, not on $\mu_a^b$ alone:

$$D(\lambda) = \log(1/I)_{ac+dc} - \log(1/I)_{dc} = \Delta V \frac{\bar{l}}{V_T}(\mu_a^b - \mu_a^t) \quad (3)$$

Figure 2:
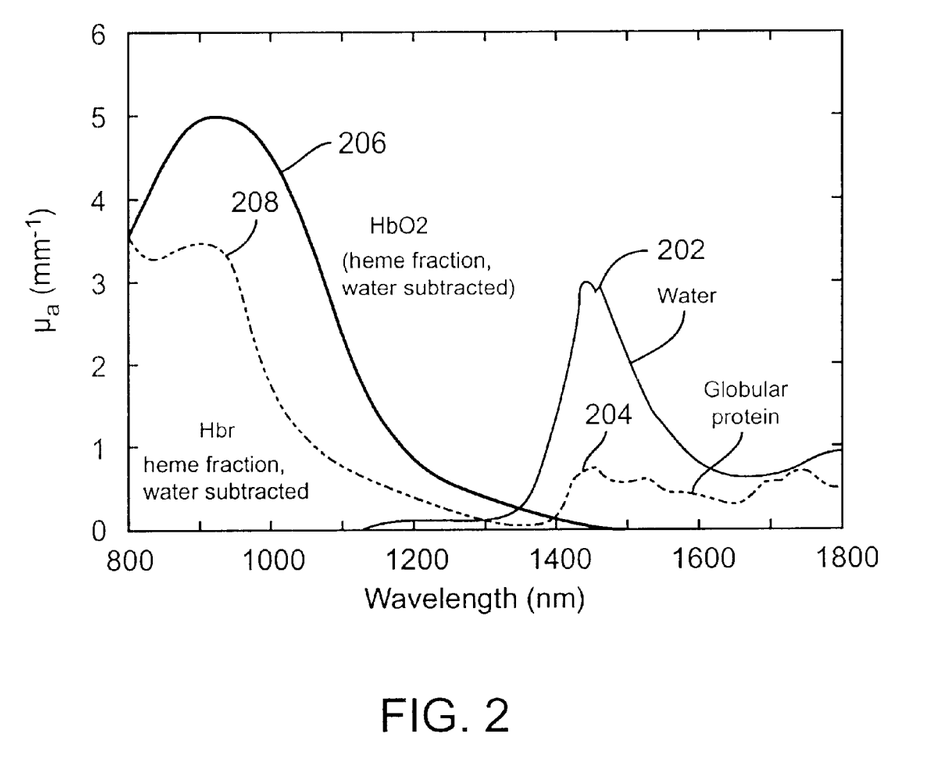
FIG. 2 is a graph of the near-infrared absorption spectra of the compounds having the major influence on the transcutaneous measurement of hematocrit.

Hemoglobin, water, and the plasma proteins are the main contributors to the absorption of near-infrared light in blood. FIG. 2 shows the absorption spectra of water 202, globular protein 204, and the oxygenated 206 and deoxygenated 208 forms of hemoglobin ($HbO_2$ and Hb) in the band of wavelengths between 800 and 1800 nm. It is possible to choose wavelengths at which absorption by the plasma proteins is negligible compared to absorption by water and hemoglobin. For such wavelengths, the absorption coefficient of the blood equals approximately $$\mu_a^b = 0.34 H \mu_a^{Hb} + (1 - 0.34H - f_{pp})\mu_a^w,$$

where H is the hematocrit, $\mu_a^w$ is the absorption coefficients of water, and $\mu_a^{Hb}$ is the sum of the absorption coefficients of the two forms of hemoglobin; $f_{pp}$ is the plasma protein fraction and the factor 0.34 is the fraction of the red cell volume occupied by hemoglobin (assumed constant). At wavelengths at which absorption by proteins and lipids can be neglected, the absorption coefficient of extravascular tissue, which contains no hemoglobin, can be approximated as $$\mu_a^t = f_w \mu_a^w,$$

where $f_w$ is the fraction of water in the tissue. Substitution of these expressions for $\mu_a^t$ and $\mu_a^b$ into Eq. 3 yields $$D(\lambda) = \Delta V \frac{\bar{\ell}}{V_T}(0.34 H \mu_a^{Hb} + (1 - 0.34H - f_w - f_{pp})\mu_a^w) \quad (4)$$

Now suppose that a pair of wavelengths $\lambda_1$ and $\lambda_2$ is chosen such that $0.34 H \mu_a^{Hb} >> \mu_a^w$ at $\lambda_1$ and $\mu_a^w >> 0.34 H \mu_a^{Hb}$ at $\lambda_2$. By selecting wavelengths that obey this relationship, absorption at the first wavelength will be primarily due to hemoglobin and absorption at the second wavelength will be primarily due to water. The wavelengths $\lambda_1 = 805$ nm and $\lambda_2 = 1310$ nm are such a pair. Then the ratio of magnitudes of the blood pulse spectrum evaluated at these two wavelengths is approximately $$R = \frac{D(\lambda)|_{\lambda=\lambda_2}}{D(\lambda)|_{\lambda=\lambda_1}} \cong \frac{[1 - 0.34H - f_w - f_{pp}]\mu_a^w(\lambda_2)}{0.34 H \mu_a^{Hb}(\lambda_1)} \quad (5)$$

which, after rearranging, can be written as $$\frac{1}{H} \cong \frac{0.34}{1 - f_w - f_{pp}}\left(1 + R\frac{\mu_a^{Hb}(\lambda_1)}{\mu_a^w(\lambda_2)}\right) \quad (6)$$

This equation (Eq. 6) is still incomplete because it does not account for difference between the scattering coefficients of the blood and surrounding tissues, $\Delta \mu_s(\lambda)$, a variable that depends on the hematocrit and tissue water fraction according to $$\Delta \mu_s(\lambda) = \mu_s^b(\lambda) - \mu_s^t(\lambda) \quad (7)$$

$$= [H(1-H)(1.4-H)]\sigma_s^{rbc}(\lambda)/v_i - \mu_{s0}^t(\lambda)[4f_w(1-f_w)]$$

where $\mu_s^b$ and $\mu_s^t$ are the scattering coefficients of the blood and extravascular tissue, respectively and $\mu_{s0}^t$ is the magnitude of the $\mu_s^t$ for $f_w = 0.5$. The constants $\sigma_s^{rbc}$ and $v_i$ represent the scattering cross section and volume of a single red blood cell, respectively. The particular form of the function relating $\mu_s^b$ and H in Eq. 7 has been found by experiment (see Steinke and Shepherd, Applied Optics, 1988, Vol. 27, pp. 4027–4033) and the parabolic dependence of $\mu_s^t$ on $f_w$ arises from its dependence on the density of scatterers in the tissue (see Schmitt and Kumrar, Applied Optics, 1998, Vol. 37, pp. 2788–2797).

A complete expression that relates H and the measured ratio of intensity difference, R, can now be written as $$\frac{1}{H} \cong \frac{0.34}{1 - f_w - f_{pp}}\left(1 + R\frac{\mu_a^{Hb}(\lambda_1) + \Delta\mu_s(\lambda_1)}{\mu_a^w(\lambda_2) + \Delta\mu_s(\lambda_2)}\right) \quad (8)$$

with $\Delta\mu_s$ defined by Eq. 7. This equation states that the reciprocal of the hematocrit is linearly proportional to R, but the offset and slope of the relationship depends on $f_w$, the volume fraction of water in the extravascular tissue that surrounds the blood vessels in the skin, and on $f_{pp}$, the plasma protein fraction of the blood. The remaining terms are constants that represent inherent properties of the blood or the extravascular tissue. Except in extreme cases of malnutrition and certain other pathological conditions, $f_{pp}$ is controlled within narrow bounds (0.06–0.08) by feedback mechanisms within the body. Therefore, it also can be treated as a constant in most situations. On the other hand, $f_w$ varies considerably from individual to individual. The water fraction in the skin of elderly or obese patients can be low as 0.5 ; in the skin of young adults, the bulk water fraction is typically between 0.65 and 0.75, but the local water fraction can approach 1.0 in well-vascularized areas. In the face of such variations, the terms in Eq. 8 that depend on $f_w$ cannot be neglected.

Figure 3:
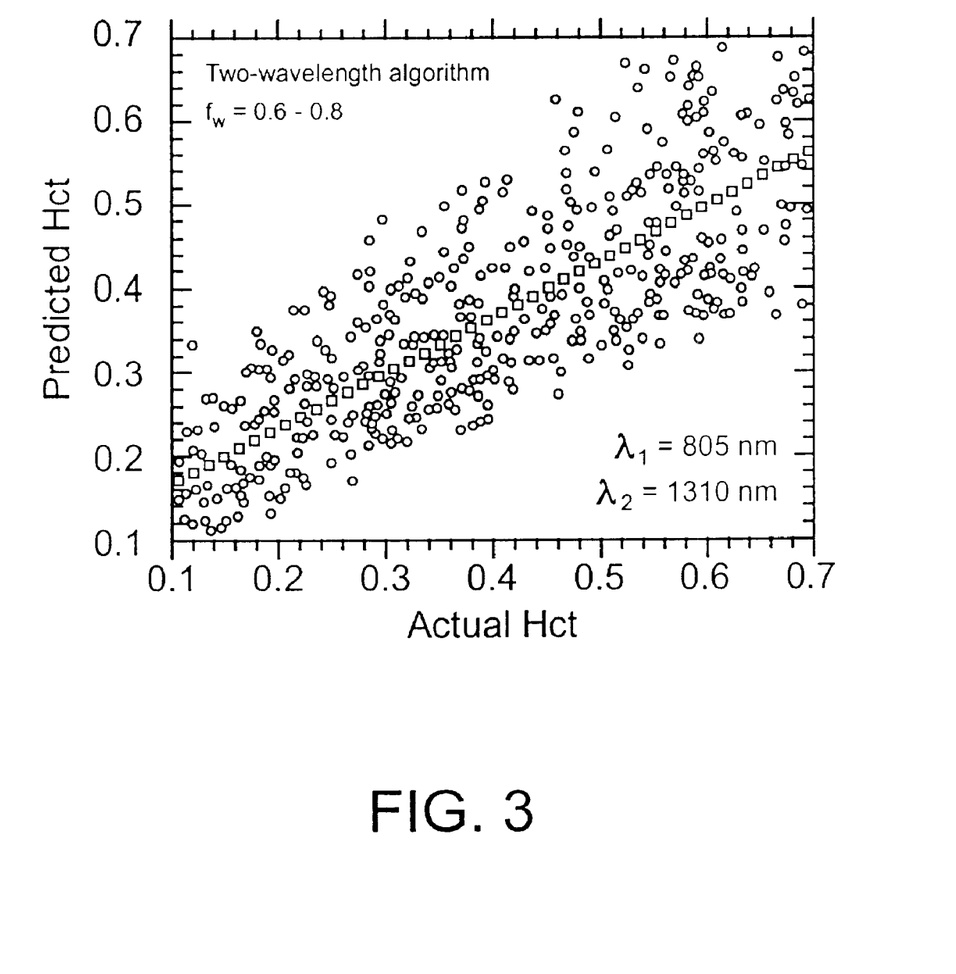
FIG. 3 is a graph of the predicted versus actual hematocrit values obtained by numerical simulation of the two-wavelength ratiometric method accounting for the normal variation in the water fraction, $f_w$.
Figure 4:
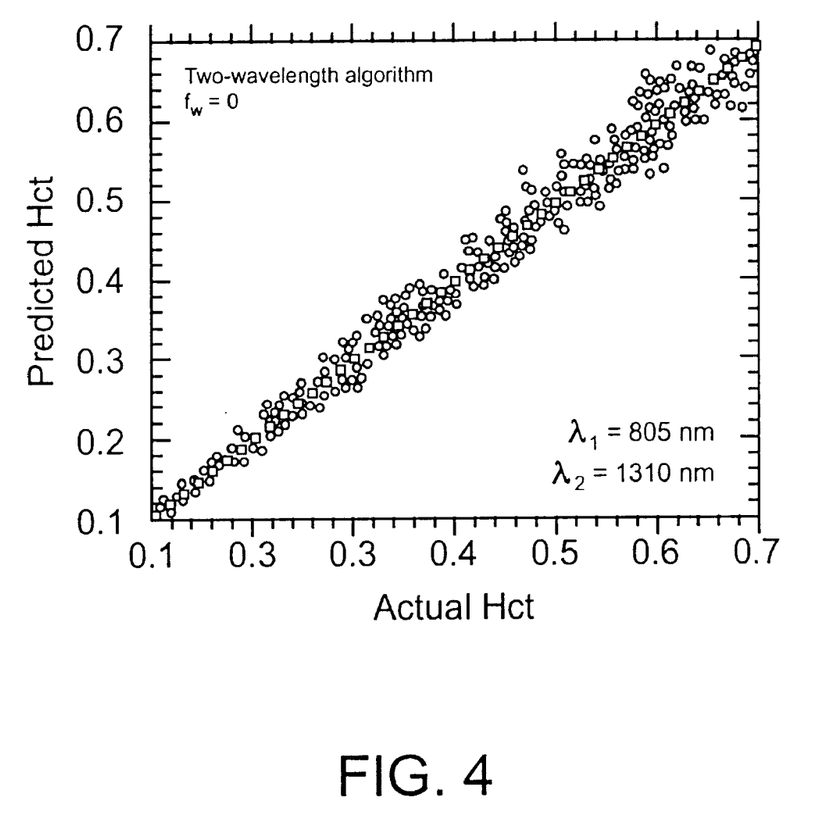
FIG. 4 is a graph of the predicted versus actual hemoglobin values obtained by numerical simulation of the two-wavelength ratiometric method with the water fraction, $f_w$, fixed at zero.

Plotted in FIG. 3 are results of numerical simulations of light propagation in skin that show the predicted errors in the measurement of hemoglobin caused by variations in the fraction of water in the extravascular tissue (see Schmitt et al., Proc. SPIE, 1996, Vol. 2678, pp. 442–453, for a description of the simulation method). The simulation accounts for the normal variations in blood volume, oxygen saturation, and skin density that one would expect to observe in healthy adults. For comparison, FIG. 4 shows the predicted errors under the same conditions, except in this case the water fraction in the extravascular tissue was fixed at zero (a case equivalent to the assumption of no tissue displacement during blood vessel expansion). The relatively large errors in the predicted values of hematocrit in FIG. 3 compared to those in FIG. 4 indicates that sensitivity to tissue water variations degrades the accuracy of the two-wavelength ratiometric method.

Figure 5:
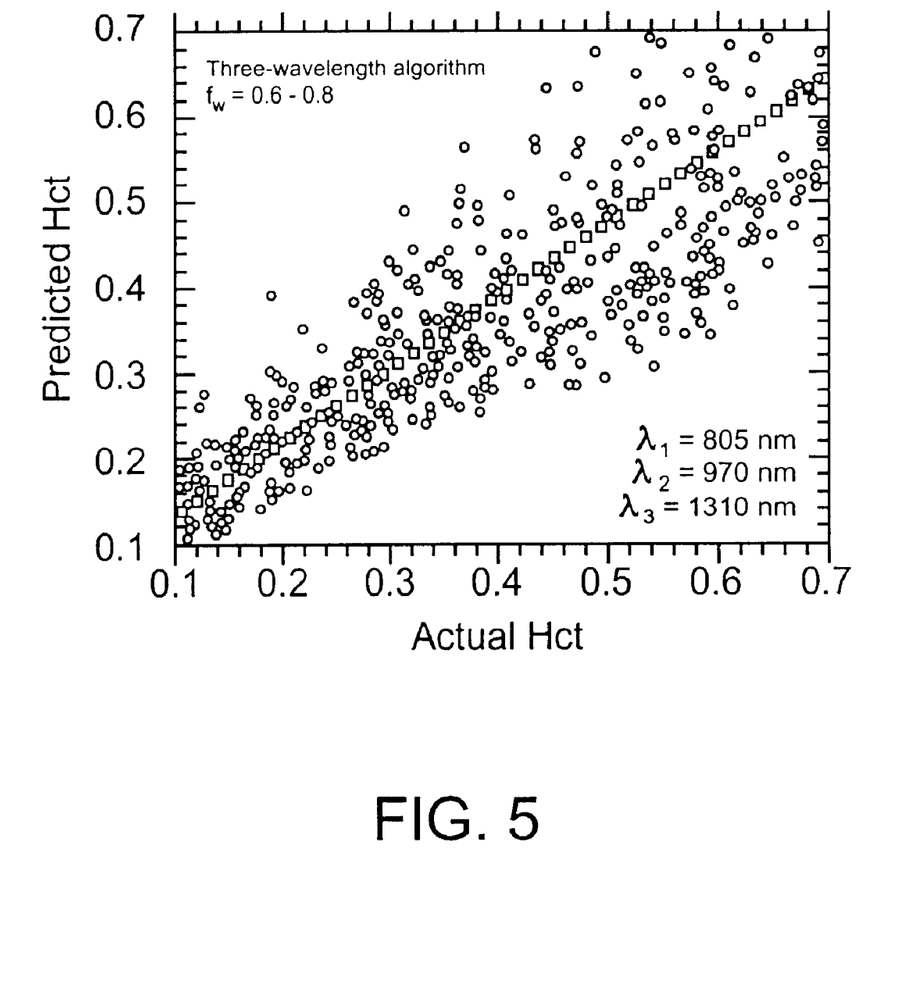
FIG. 5 is a graph of the predicted versus actual hematocrit values obtained by numerical simulation of a previously disclosed three-wavelength ratiometric method with normal variation in the water fraction, $f_w$, included.

Performing ratiometric measurements at more than two wavelengths can reduce the errors that result from changes in the optical properties of the extravascular tissue, but cannot eliminate them. FIG. 5 evaluates the performance of a three-wavelength ratiometric algorithm modeled after the algorithm suggested by Steuer et al. (U.S. Pat. No. 5,499, 627), $$\frac{1}{H} = k'\frac{D(\lambda)|_{\lambda=1310nm}}{D(\lambda)|_{\lambda=805nm}} - k''\frac{D(\lambda)|_{\lambda=970nm}}{D(\lambda)|_{\lambda=805nm}} + k''' \quad (9)$$

The regression constants k', k", and k'" used in the simulation were chosen to give the best fit between the actual and predicted hematocrits. Although somewhat improved, the predicted errors of the hematocrit measurement in FIG. 5 are still large compared to those obtained for the non-zero, fixed $f_w$ case (FIG. 3). As can be seen from FIG. 5, measuring ratios of the blood pulse spectrum at additional wavelengths does not overcome the inherent dependence of the magnitude of the spectrum on the optical properties of the extravascular tissue.

From the preceding analysis it can be appreciated that measuring the blood pulse spectrum on a body site at which $f_w$ is small and constant would improve the measurement accuracy. The earlobe, in which many of the blood vessels are embedded in adipose tissue, comes closest to satisfying this requirement. However, in many applications the earlobe is an inconvenient measurements site and its adipose content varies from individual to individual.

A more robust approach to reducing the errors caused by tissue water variations is to measure $f_w$ and use the measured value in the prediction equation (Eq. 8). In a preferred embodiment of the present invention, the tissue water fraction is derived from diffuse light intensities measured at a set of wavelengths within the same band of near-infrared wavelengths (800–1800 nm) used to measure the blood pulse spectrum. Intensity ratios are recorded when the skin in the resting state (before blood volume expansion) and are then log-transformed and combined according to $$f_w = k_1 \log\left(\frac{I(\lambda_3)}{I(\lambda_4)}\right)_{dc} + k_2 \log\left(\frac{I(\lambda_5)}{I(\lambda_6)}\right)_{dc} + k_3 \qquad (10)$$

For specific sets of wavelengths, $\lambda_3$–$\lambda_6$ and constants $k_1$-$k_3$, this general expression enables precise measurement of the absolute tissue water fraction $f_w$. The values of the constants can be determined from mathematical models or by empirical calibration. The results of numerical simulations suggest that $f_w$ values derived from Eq. 10 for $\lambda_3$=850 nm, $\lambda_4$=1370 nm, $\lambda_5$=1250 nm, $\lambda_6$=1140 nm, are accurate to within ±1% over the physiological range of blood volume and scattering variations. One important feature of this particular choice of wavelengths is that intensities measured at the longest and shortest wavelengths $\lambda_3$=850 nm, $\lambda_4$=1370 nm, can also be used in the calculation of the ratio R at wavelengths $\lambda_1$ and $\lambda_2$ in Eq. 5. That is, for $\lambda_1$=$\lambda_4$=1370 nm and $\lambda_2$=$\lambda_3$=850 nm, measurements at four rather than six wavelengths are required to determine the hematocrit. Reducing the number of measurement wavelengths lowers the manufacturing cost of portable devices that employ discrete light-emitting diodes as light sources. Another advantage of overlapping the wavelengths used to measure R and $f_w$ is that differences in the optical path lengths that determine the geometry of sample volume are minimized. Eq. 10 is not, however, the only possible algorithm for determination of tissue water fraction. Other methods and algorithms, including those disclosed by the inventor herein in a application Ser. No. 09/810,918 assigned to the assignee herein, and titled: Device and Method for Monitoring Body Fluid and Electrolyte Disorders, which is hereby incorporated herein by reference, will also yield accurate estimates of tissue water fraction.

Although the key concepts that underlie the disclosed methods for noninvasive Hct measurement are embodied in Eqs. 8, 10 and those methods and algorithms disclosed in the above referenced patent application Ser. No. 09/810,918 (Device and Method for Monitoring Body Fluid and Electrolyte Disorders, the design of apparatus with which the required intensities are measured also plays an equally crucial role. In particular, the magnitudes of the optical signals from which R and $f_w$ are derived must be large enough to ensure minimal interference from electronic noise as well as from noise related to physiological variables, which include body movements and spatial heterogeneity in local blood flow.

Figure 6:
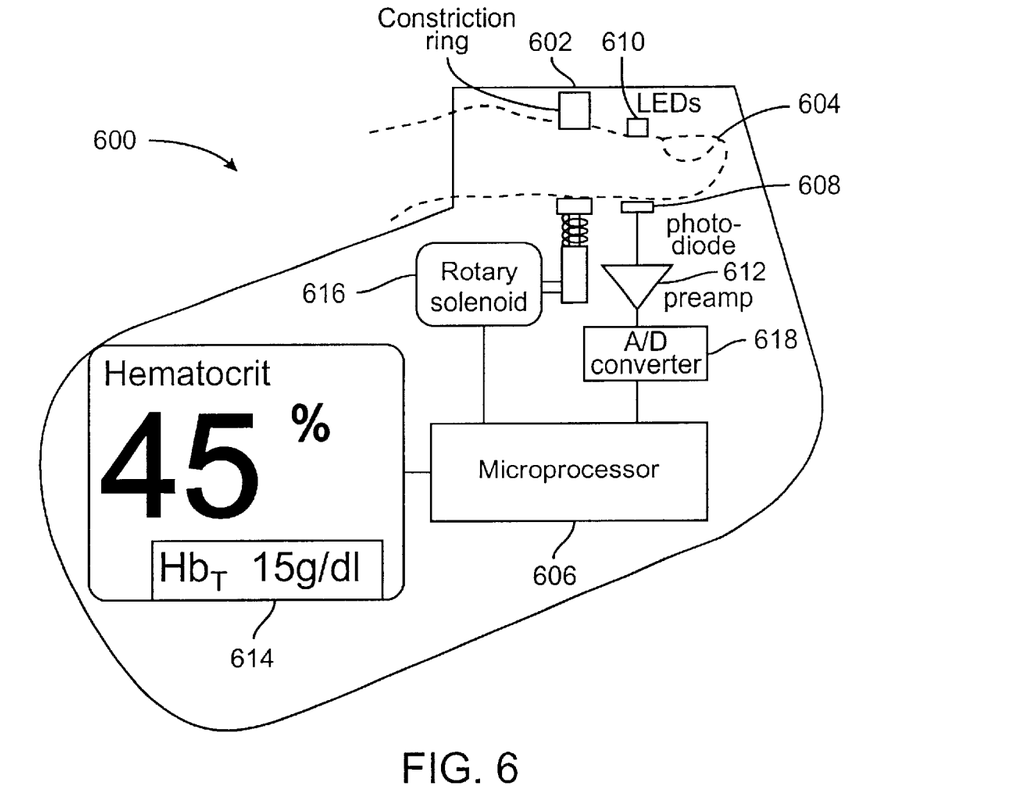
FIG. 6 is a block diagram of a handheld apparatus for noninvasive measurement and display of hematocrit and total hemoglobin concentration in the blood.

The apparatus depicted in FIG. 6 has several features that facilitate the accurate measurement of Hct noninvasively. The solenoid-operated clamp 602 occludes the venous return from the finger 604 by applying pressure around the circumference of the finger 604 via the rotary solenoid 616 which is coupled to the clamp 602. The applied pressure is adjusted to a level just above the value of the diastolic blood pressure. As a result, the arterial blood continues to flow unimpeded into the fingertip until the flow stops when the blood vessels distend to their maximum filling volumes. Microprocessor 606 controls the timing of the occlusion cycle, data acquisition and processing to determine the value of Hct. Before the start of occlusion cycle, the microprocessor-controlled data acquisition system begins to record the electrical signals generated by photodetector 608. The photodetector 608 is mounted on compressible rubber pad (not shown) or spring-loaded post (not shown) which maintains contact with the palmar side of the finger 604 without restricting its expansion during the occlusion period. Before the signals are digitized by the analog to digital (A/D) converter 618, they are amplified by the preamp 612 and normalized to ensure their proportionality to the intensities of the light transmitted through the finger from the light-emitting diode (LED) sources 610, which are mounted close together on the same substrate (not shown). The signals are multiplexed by turning the LEDs on in sequence to permit near-simultaneous measurement of the intensities by a single photodetector. After approximately five seconds have elapsed, the clamp 602 releases automatically and the finger 604 can be removed. A short time later, Hct is displayed on the display panel 614 as a percentage along with the calculated value of $Hb_T$ in g/dl. In one embodiment, the display panel 614 is a built-in liquid-crystal (LCD) panel.

In alternate embodiments, light emission sources and optics may include sources other than LEDs such as incandescent light sources or white light sources which are tuned to emit radiation at appropriate wavelengths.

In one embodiment of the invention, a miniature solenoid 616 for performing the occlusion, the light emission 610 and detection optics 608, processing device 606, and display 614 are all contained within a handheld device 600. Actuation of the solenoid triggers the start of measurement cycle. The difference between the logarithms of the intensities measured at specific wavelengths in the band between 800–1000 nm in which hemoglobin is the dominant absorber and between 1250–1600 nm in which water is the dominant absorber are recorded immediately before and immediately after occlusion. To calculate the hematocrit, these measured differences are combined with an estimate of the extravascular water fraction derived from the weighted sum of the derivatives of the transmittance or reflectance spectra of the tissue measured in an overlapping band of wavelengths. Alternate embodiments use substitute occlusion means such as a pneumatic or hydraulic-operated clamps. Additional alternate embodiments use other algorithms for determining the tissue water fraction as described above.

Figure 7:
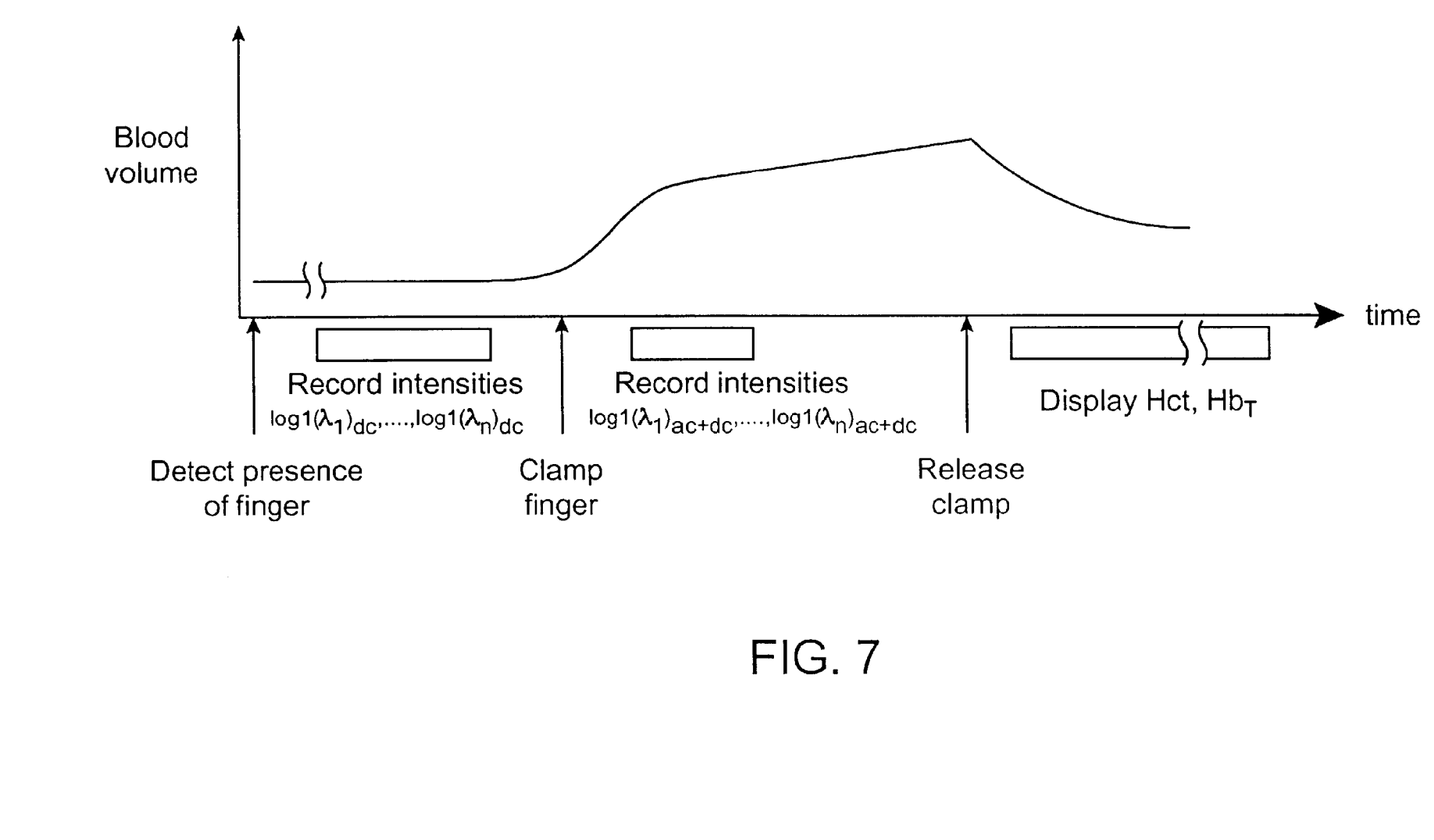
FIG. 7 is a timing diagram of the data acquisition process used to measure light intensities for determination of hematocrit by the venous-occlusion method.

FIG. 7 shows the timing of the data acquisition and processing during the measurement cycle. A pressure transducer senses the presence of a finger and actuates the occlusion device which in turn starts the data acquisition sequence. The sequence starts automatically after the microprocessor has detected the presence of the finger. Before the solenoid is activated, the LEDs are turned on to record the average values of the before-expansion diffuse transmittances $\log[I(\lambda_1)]_{dc}, \ldots, \log[I(\lambda_n)]_{dc}$ over an interval of 0.5–1.0 second. These dc measurements are used both for the before venous-expansion values to determine Hct as well as measurements of tissue water. Recording of the transmittances proceeds continuously at a fast sampling rate after the solenoid activates and the finger clamp closes. The after-expansion transmittances $\log[I(\lambda_1)]_{ac+dc}, \ldots, \log[I(\lambda_n)]_{ac+}$ $dc$ are recorded as averaged values calculated over an interval of one-half second or less just prior to the maximum of the blood volume expansion, as determined from the magnitude of $D(\lambda)|_{\lambda=\lambda_1}$. It is important to perform the after-expansion measurements within an interval no longer than a few seconds after venous blood flow from the finger ceases, because the elevated venous pressure can lead to desaturation of the blood and loss of water through the capillaries, factors that may influence the accuracy of the hemoglobin measurement. The fractional change in the blood volume induced by the venous occlusion is typically an order of magnitude greater than that produced by normal arterial pulsations. This signal enhancement, combined with the reduction of noise that results from longer averaging times, gives the venous-occlusion method a significant advantage over optical plethysmography based on the measurement of natural blood pulsations. An additional advantage of the venous-occlusion method is that it facilitates the detection and removal of any asynchronous noise component of the time-varying intensities caused by the sudden expansion of the blood vessels. Ballistic waves generated by expanding vessels can temporarily alter the scattering coefficient of the bulk tissue and produce optical artifacts. Similar artifacts associated with natural arterial blood pulsations are harder to remove because they occur at almost the same time as the upstroke of the optical plethysmogram. The change in the blood volume brought about as a result of venous occlusion will drown out any such ballistic waves and hence minimize any potential optical artifacts. The design of the device and the microprocessor integrates the method and apparatus for reducing the effect of noise on measuring physiological parameters as described in U.S. Pat. No. 5,853,364, assigned to Nellcor Puritan Bennett, Inc., now a division of the assignee of the present invention, the entire disclosure of which is hereby incorporated herein by reference. Additionally, the design of the device and the microprocessor also integrates the electronic processor as described in U.S. Pat. No. 5,348,004, assigned to Nellcor Incorporated, now a division of the assignee of the present invention, the entire disclosure of which is hereby incorporated herein by reference.

Figure 8:
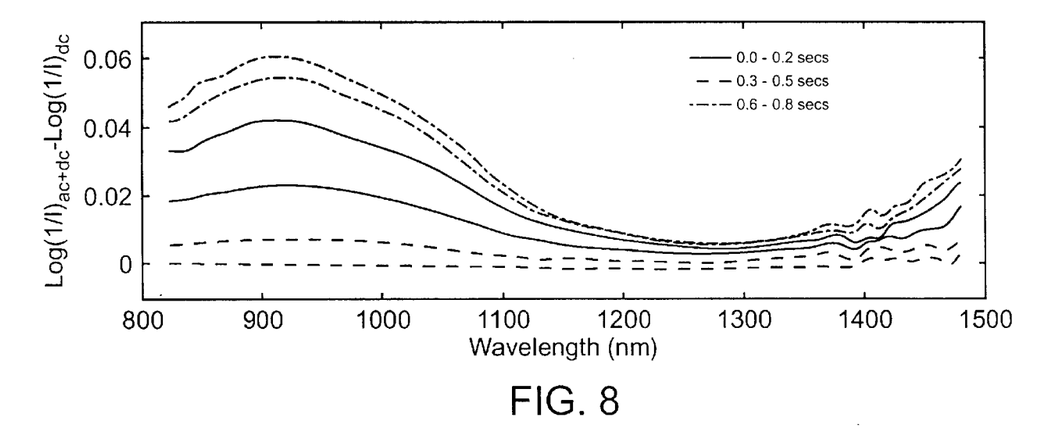
FIG. 8 is a graph of the pulse spectra measured from the finger of a healthy adult subject.
Figure 9:
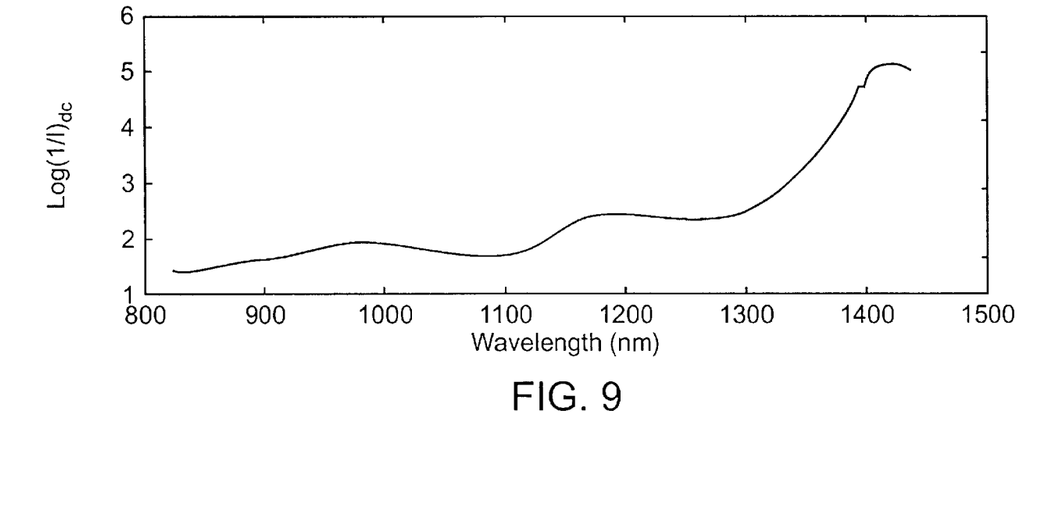
FIG. 9 is a graph of the dc spectrum measured from the finger of a healthy adult subject.

FIGS. 8 and 9 show examples of a set of pulse spectra $D(\lambda)$ measured as a function of time shortly after occlusion of the blood flow to the index finger, along with the corresponding $\log[I(\lambda)]_{dc}$ spectrum of the finger. The magnitudes of these spectra at selected wavelengths contain the information required for the determination of Hct according to Eq. 8 and Eq. 10 and other algorithms used to measure tissue water as described above.

Figure 10:
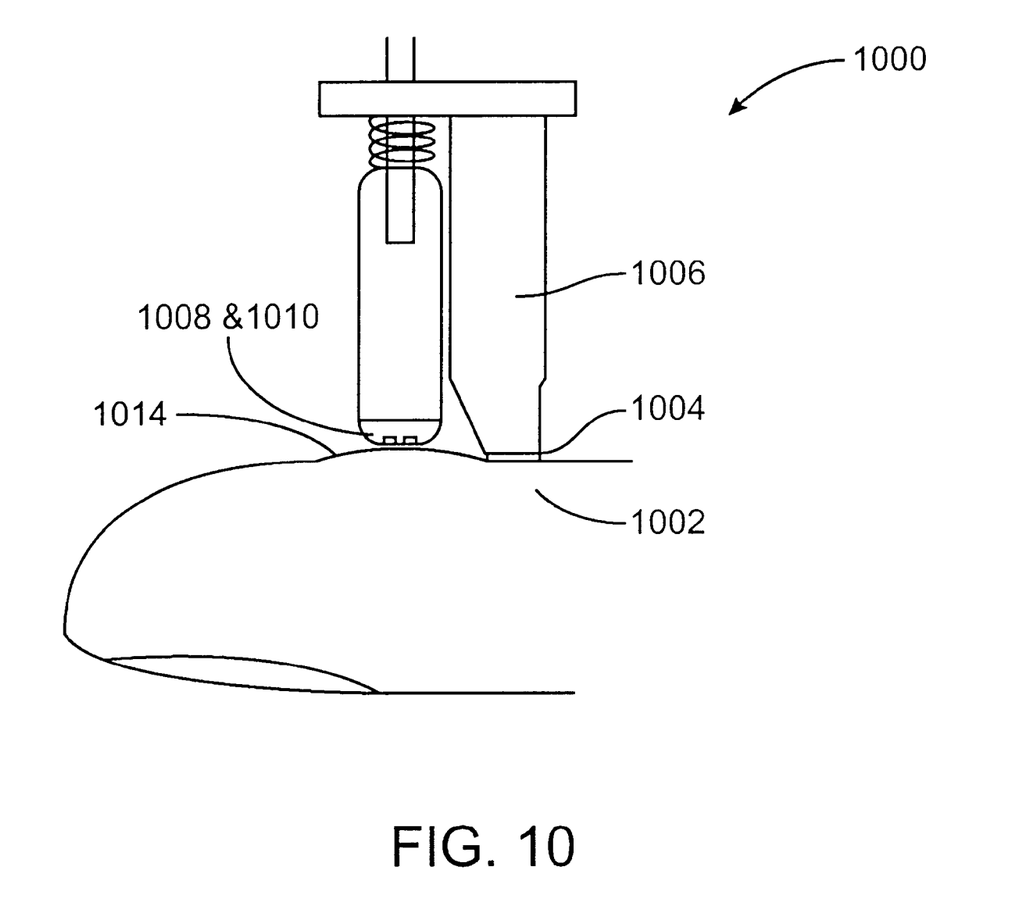
FIG. 10 is a diagram of a mechanically operated reflectance sensor for rapid measurement of hematocrit via the venous-occlusion method.

An additional embodiment of the device is shown in FIG. 10. FIG. 10 shows a manual version of a reflectance sensor 1000 designed for application to the tip of a finger or toe. This embodiment relies on partial, instead of full, venous occlusion from any well-perfused area of the skin by applying compression to an adjacent area with an appropriately shaped probe. When the skin 1002 is compressed, a pressure transducer 1004 mounted on the end of the occluder 1006 senses the applied pressure and controls the timing of the data acquisition. As the blood volume increases in the area of the skin 1002 proximal to the occluder 1006, the light sources 1008 and detector 1010 mounted in a miniature spring-loaded probe 1012 record the decrease in the diffusely reflected intensity during the occlusion cycle. This embodiment is more suitable for rapid screening for anemia in a large population of subjects.

In the embodiment depicted in FIG. 10, the light impinges on and is collected from the skin directly by mounting the detector and light sources at the tip of the sensor. Likewise, in the automatic embodiment shown in FIG. 6, the light emission and detection are positioned locally in the device housing. In alternate embodiments of the automatic and manual versions of the device, the light emission and detection are conducted to and from a remote unit containing the sources and the photodetector via optical fibers.

Individuals familiar with the art of spectral processing will realize that full-spectrum processing methods, such as partial-least squares analysis and principal component regression, may also be applied to the measured spectra to improve the accuracy of the hemoglobin estimates. Additional embodiments which implement these techniques, employ a white-light source and a grating detector to measure the transmittances or reflectances from blood-perfused tissue over a continuous range of wavelengths.

A number of variations of the apparatus will be apparent to those skilled in the art of tissue optics. Reflected rather than transmitted intensities can be measured by placing the light sources on the same side of the blood-perfused tissue as the light detector. The separation between the sources and detectors is an important variable that influences the probing depth as well as the sensitivity of the measured intensities to scattering variations. By operating the apparatus in the reflection mode with a distance of 2–3 millimeters between the light sources and detectors, the effective optical path can be confined to the well-perfused dermal layer. Operation in the reflection mode has the additional benefit of permitting measurements to be made on parts of the body besides the appendages. Moreover, light sources or light emission optics other then LED's including and not limited to narrowband light sources appropriately tuned to the desired wavelengths and associated light detection optics may be placed within the probe housing which is placed near the tissue location or may be positioned within a remote unit; and which deliver light to and receive light from the probe location via optical fibers. These equivalents and alternatives along with obvious changes and modifications are intended to be included within the scope of the present invention. Accordingly, the foregoing disclosure is intended to be illustrative, but not limiting, of the scope of the invention which is set forth in the following claims.

What is claimed is:

1. A device for measuring hematocrit values using optical spectrophotometry comprising:

a probe housing configured to be placed proximal to a tissue location which is being monitored;

an occlusion device connected to said housing and configured to magnify the fractional change in the vascular blood volume to a value greater than said fractional change produced by normal arterial pulsations;

light emission optics connected to said housing and configured to direct radiation at said tissue location;

light detection optics connected to said housing and configured to receive radiation from said tissue location;

a processing device connected to said housing and configured to process radiation from said light emission optics and said light detection optics to compute a tissue water fraction and compute said hematocrit values, using said tissue water fraction.

2. The device of claim 1, further comprising a display device connected to said probe housing and configured to display said hematocrit values.

3. The device of claim 1, further comprising means for measuring hemoglobin.

4. The device of claim 1, further comprising a pressure transducer connected to said housing and positioned to be placed adjacent to said tissue location, and configured to interface with said processing device and said occlusion device to provide an input to said processing device to control the timing of the data acquisition by said processing device.

5. The device of claim 1, wherein said light emission optics are tuned to emit radiation at at least a first and a second wavelength, where said at least first wavelength is within a band of wavelengths where hemoglobin is the dominant absorber and where said at least second wavelength is within a band of wavelengths where water is the dominant absorber.

6. The device of claim 1, wherein said light emission optics are tuned to emit radiation at at least a first and a second wavelength, where said at least first wavelength is within a band of wavelengths in the range of approximately 800–1000 nm and where said at least second wavelength is within a band in the range of approximately 1250–1600 nm.

7. The device of claim 1, wherein said light emission optics are tuned to emit radiation at at least a first and a second wavelength, where said first and said second wavelengths are related to each other such that $0.34 H \mu_a^{Hb} \gg \mu_a^w$ at said first wavelengths and $\mu_a^w \gg 0.34 H \mu_a^{Hb}$ at said second wavelength, where H is the hematocrit value, $\mu_a^{Hb}$ is the sum of the absorption coefficient of the two forms of hemoglobin, and $\mu_a^w$ is the absorption coefficient of water.

8. The device of claim 1, wherein said light emission optics are tuned to emit radiation at at least a first and a second wavelength, where said at least first wavelength is in a range approximately between and including 805 to 850 nm and said at least second wavelength is in a range approximately between and including 1310 to 1370 nm.

9. The device of claim 1, wherein said light emission optics and said light detection optics are mounted within said probe housing and positioned with appropriate alignment to enable detection in a transmissive mode.

10. The device of claim 1, wherein said light emission optics and said light detection optics are mounted within said probe housing and positioned with appropriate alignment to enable detection in a reflective mode.

11. The device of claim 1, wherein said light emission optics and said light detection optics are placed within a remote unit and which deliver light to and receive light from said probe housing via optical fibers.

12. The device of claim 1, wherein said light emission optics comprise at least one of a (a) incandescent light source, (b) narrowband light source, wherein a narrowband light source comprises one of a light emitting diode ("LED") and a filtered white light source.

13. The device of claim 1, wherein said processing device receives at least two sets of optical measurements, where the at least first set of optical measurements corresponds to the detection of light whose absorption is primarily due to hemoglobin, and where the at least second set of optical measurements corresponds to the detection of light whose absorption is primarily due to water, and where a combination of said at least two sets of optical measurements provides a measure of said hematocrit value.

14. The device of claim 1, wherein said processing device:

receives at least two sets of optical measurements at an at least a first and a second wavelength, where for each wavelength two optical measurements are obtained corresponding to measurements before and after a venous occlusion conducted by said occlusion device to obtain before and after occlusion measurements at each wavelength;

combines said before and after occlusion measurements at each wavelength to determine a blood pulse spectrum at each wavelength;

combines said blood pulse spectra at each wavelength to obtain a ratio of said blood pulse spectra; and combines said ratio with measurements of tissue water fractions to determines the concentration of hemoglobin in the blood.

15. The device of claim 1, wherein said processing device determines hematocrit based on optical measurements such that $$\frac{1}{H} \cong \frac{0.34}{1 - f_w - f_{pp}} \left( 1 + R \frac{\mu_a^{Hb}(\lambda_1) + \Delta \mu_s(\lambda_1)}{\mu_a^w(\lambda_2) + \Delta \mu_s(\lambda_2)} \right), \text{ where:}$$

H is the hematocrit value;

$f_w$ is the tissue water fraction;

$f_{pp}$ is the plasma protein fraction;

R is the ratio of magnitudes of the blood pulse spectrum;

$\mu_a^{Hb}(\lambda_1)$ is the sum of the absorption coefficient of the two forms of hemoglobin at a first wavelength;

$\mu_a^w(\lambda_2)$ is the absorption coefficient of water at a second wavelength;

$\Delta \mu_s(\lambda_1)$ is the difference between the scattering coefficients of the blood and surrounding tissue at a first wavelength;

$\Delta \mu_s(\lambda_2)$ is the difference between the scattering coefficients of the blood and surrounding tissue at a second wavelength; and 0.34 is the fraction of the red cell volume occupied by hemoglobin, which is assumed to be constant.

16. A device for measuring hematocrit values using optical spectrophotometry comprising:

a probe housing configured to be placed proximal to a tissue location which is being monitored;

an occlusion device connected to said housing and configured to magnify the fractional change in the vascular blood volume to a value greater than said fractional change produced by normal arterial pulsations;

light emission optics connected to said housing and configured to direct radiation at said tissue location, wherein said light emission optics comprise at least one of a (a) incandescent light source, (b) white light source and (c) light emitting diodes ("LEDs") which are tuned to emit radiation at at least a first and a second wavelength, where said at least first wavelength is within a band of wavelengths where hemoglobin is the dominant absorber and where said at least second wavelength is within a band where water is the dominant absorber;

a photodiode connected to said housing and configured to receive radiation from said tissue location;

a processing device connected to said housing and configured to process radiation from said light emission optics and said light detection optics to compute said hematocrit values, wherein said processing device:

receives at least two sets of optical measurements at an at least a first and a second wavelength, where for each wavelength two optical measurements are obtained corresponding to measurements before and after a venous occlusion conducted by said occlusion device, to obtain before and after occlusion measurements at each wavelength;

combines said before and after measurements at each wavelength to determine a blood pulse spectrum at each wavelength;

combines said blood pulse spectra at each wavelength to obtain a ratio of said blood pulse spectra;

combines said ratio with measurements of tissue water fractions to determines the blood hematocrit value, such that $$\frac{1}{H} \cong \frac{0.34}{1 - f_w - f_{pp}}\left(1 + R\frac{\mu_a^{Hb}(\lambda_1) + \Delta\mu_s(\lambda_1)}{\mu_a^w(\lambda_2) + \Delta\mu_s(\lambda_2)}\right), \text{ where:}$$

H is the hematocrit value;
$f_w$ is the tissue water fraction;
$f_{pp}$ is the plasma protein fraction;
R is the ratio of magnitudes of the blood pulse spectrum;
$\mu_a^{Hb}(\lambda_1)$ is the sum of the absorption coefficient of the two forms of hemoglobin at a first wavelength;
$\mu_a^w(\lambda_2)$ is the absorption coefficient of water at a second wavelength;
$\Delta\mu_s(\lambda_1)$ is the difference between the scattering coefficients of the blood and surrounding tissue at a first wavelength;
$\Delta\mu_s(\lambda_2)$ is the difference between the scattering coefficients of the blood and surrounding tissue at a second wavelength; and
0.34 is the fraction of the red cell volume occupied by hemoglobin, which is assumed to be constant.

17. The device of claim 16, further comprising a pressure transducer connected to said housing and positioned to be placed adjacent to said tissue location, and configured to interface with said processing device and said occlusion device to provide an input to said processing device to control the timing of the data acquisition by said processing device.

18. The device of claim 16, wherein said light emission optics are tuned to emit radiation at at least a first and a second wavelength, where said at least first wavelength is within a band of wavelengths in the range of approximately 800–1000 nm and where said at least second wavelength is within a band in the range of approximately 1250–1600 nm.

19. A method of measuring a percent hematocrit near a tissue location using optical spectrophotometry comprising:
placing a probe housing proximal to said tissue location;
occluding the venous blood flow adjacent to said tissue location;
emitting radiation at at least two wavelengths using light emission optics configured to direct radiation at said tissue location;
detecting radiation using light detection optics configured to receive radiation from said tissue location;
processing said radiation from said light emission and said light detection optics using a processing device;
computing said percent hematocrit, where said percent hematocrit is determined by:
receiving at least two sets of optical measurements at an at least a first and a second wavelength, where for each wavelength two optical measurements are obtained corresponding to measurements before and after a venous occlusion, to obtain before and after occlusion measurements at each wavelength;
combining said before and after measurements at each wavelength;
determining a blood pulse spectrum at each wavelength;
obtaining a ratio of said blood pulse spectra;
combining said ratio with measurements of tissue water fractions; and
determining said percent hematocrit value such that $$\frac{1}{H} \cong \frac{0.34}{1 - f_w - f_{pp}}\left(1 + R\frac{\mu_a^{Hb}(\lambda_1) + \Delta\mu_s(\lambda_1)}{\mu_a^w(\lambda_2) + \Delta\mu_s(\lambda_2)}\right), \text{ where:}$$

H is the hematocrit value;
$f_w$ is the tissue water fraction;
$f_{pp}$ is the plasma protein fraction;
R is the ratio of magnitudes of the blood pulse spectrum;
$\mu_a^{Hb}(\lambda_1)$ is the sum of the absorption coefficient of the two forms of hemoglobin at a first wavelength;
$\mu_a^w(\lambda_2)$ is the absorption coefficient of water at a second wavelength;
$\Delta\mu_s(\lambda_1)$ is the difference between the scattering coefficients of the blood and surrounding tissue at a first wavelength;
$\Delta\mu_s(\lambda_2)$ is the difference between the scattering coefficients of the blood and surrounding tissue at a second wavelength; and
0.34 is the fraction of the red cell volume occupied by hemoglobin, which is assumed to be constant.

20. The method of claim 19, wherein said first wavelength is chosen from within a band of wavelengths in the range of approximately 800–1000 nm and where said second wavelength is chosen from within a band of wavelengths in the range of approximately 1350–1600 nm.

21. The method of claim 19, wherein said first and said second wavelengths are related to each other such that $0.34H\mu_a^{Hb} >> \mu_a^w$ at said first wavelengths and $\mu_a^w >> 0.34H\mu_a^{Hb}$ at said second wavelength, where
H is the hematocrit value,
$\mu_a^{Hb}$ is the sum of the absorption coefficient of the two forms of hemoglobin, and
$\mu_a^w$ is the absorption coefficient of water.

22. The method of claim 19, wherein said first and second wavelengths are approximately between and including 805 to 850 nm and approximately between and including 1310 to 1370 nm respectively.

23. A method of computing percent hematocrit based on optical measurements, wherein said percent hematocrit is determined such that $$\frac{1}{H} \cong \frac{0.34}{1 - f_w - f_{pp}}\left(1 + R\frac{\mu_a^{Hb}(\lambda_1) + \Delta\mu_s(\lambda_1)}{\mu_a^w(\lambda_2) + \Delta\mu_s(\lambda_2)}\right), \text{ where:}$$

H is the hematocrit value;
$f_w$ is the tissue water fraction;
$f_{pp}$ is the plasma protein fraction;
R is the ratio of magnitudes of the blood pulse spectrum;
$\mu_a^{Hb}(\lambda_1)$ is the sum of the absorption coefficient of the two forms of hemoglobin at a first wavelength;
$\mu_a^w(\lambda_2)$ is the absorption coefficient of water at a second wavelength;
$\Delta\mu_s(\lambda_1)$ is the difference between the scattering coefficients of the blood and surrounding tissue at a first wavelength;

$\Delta\mu_s(\lambda_2)$ is the difference between the scattering coefficients of the blood and surrounding tissue at a second wavelength; and 0.34 is the fraction of the red cell volume occupied by hemoglobin, which is assumed to be constant.

24. The method of claim 23, wherein said first wavelength is chosen from within a band of wavelengths in the range of approximately 800–1000 nm and where said second wavelength is chosen from within a band of wavelengths in the range of approximately 1350–1600 nm.

25. The method of claim 23, wherein said first and said second wavelengths are related to each other such that $0.34 H \mu_a^{Hb} \gg \mu_a^w$ at said first wavelengths and $\mu_a^w \gg 0.34 H \mu_a^{Hb}$ at said second wavelength, where H is the hematocrit value, $\mu_a^{Hb}$ is the sum of the absorption coefficient of the two forms of hemoglobin, and $\mu_a^w$ is the absorption coefficient of water.

26. The method of claim 23, wherein said first and second wavelengths are approximately between and including 805 to 850 nm and approximately between and including 1310 to 1370 nm respectively.

27. A method of measuring a percent hematocrit near a tissue location using optical spectrophotometry comprising:

irradiating said tissue location and processing received signals from said tissue location to measure tissue water;

occluding the venous blood flow adjacent to said tissue location;

repeat irradiating said tissue location;

detecting radiation from said tissue following said repeat irradiating; and calculating hematocrit values using tissue water measurements.

* * * * *